United States Patent
Williams et al.

(10) Patent No.: US 10,709,630 B2
(45) Date of Patent: Jul. 14, 2020

(54) SPINE TABLE POSITIONER PAD WITH PRESSURE SENSING AND COOLING FEATURES

(71) Applicant: Allen Medical Systems, Inc., Batesville, IN (US)

(72) Inventors: Joshua A. Williams, West Harrison, IN (US); Benjamin E. Howell, Fuquay-Varina, NC (US); Todd P. O'Neal, Fairfield, OH (US); Jeffrey C. Marrion, Acton, MA (US); Yongji Fu, Harrison, OH (US); Joshua C. Hight, Sommerville, MA (US); Andrew Sennett, Hanover, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 470 days.

(21) Appl. No.: 15/181,769

(22) Filed: Jun. 14, 2016

(65) Prior Publication Data
US 2016/0361217 A1  Dec. 15, 2016

Related U.S. Application Data

(60) Provisional application No. 62/175,607, filed on Jun. 15, 2015.

(51) Int. Cl.
*A61G 13/00* (2006.01)
*A61B 6/04* (2006.01)
(Continued)

(52) U.S. Cl.
CPC ........ *A61G 13/0036* (2013.01); *A61B 6/0407* (2013.01); *A61G 7/05738* (2013.01);
(Continued)

(58) Field of Classification Search
CPC ............ A61G 13/0036; A61G 13/0054; A61G 13/1265; A61G 7/05738; A61G 13/08;
(Continued)

(56) References Cited

U.S. PATENT DOCUMENTS 3,644,950 A * 2/1972 Lindsay, Jr. ........... A61G 7/057
  297/DIG. 3
3,757,362 A * 9/1973 Bowlin ................ A47C 21/044
  5/421
(Continued)

FOREIGN PATENT DOCUMENTS

CN  203663009 U   6/2014
GB   2489118 A    9/2012
(Continued)

OTHER PUBLICATIONS

EP Communication dated Oct. 17, 2017 for EP Application No. 16174273.9.
(Continued)

*Primary Examiner* — Nicholas F Polito
*Assistant Examiner* — Alexis Felix Lopez
(74) *Attorney, Agent, or Firm* — Dinsmore & Shohl LLP

(57) ABSTRACT

Embodiments include a modular support pad having a support cushion, a fluid-filled bladder coupled to an electronic pressure sensor for sensing a fluid pressure within the fluid-filled bladder, and a ticking surrounding the support cushion and the fluid-filled bladder and providing a person support surface between the fluid-filled bladder and a person. Other embodiments include a modular support pad having a support cushion, a bladder coupled to an electronic pump for circulating a cooling fluid within the bladder, and a ticking surrounding the support cushion and the bladder and providing a person support surface between the bladder and a person. Methods of sensing pressure applied by a support pad are also described.

5 Claims, 3 Drawing Sheets

(51) Int. Cl.
*A61G 7/057* (2006.01)
*A61G 13/08* (2006.01)
*A61G 13/12* (2006.01)

(52) U.S. Cl.
CPC .......... *A61G 13/0054* (2016.11); *A61G 13/08* (2013.01); *A61G 13/1265* (2013.01); *A61G 2203/34* (2013.01); *A61G 2210/50* (2013.01); *A61G 2210/70* (2013.01)

(58) Field of Classification Search
CPC ............ A61G 2210/70; A61G 2210/50; A61G 2203/34; A61B 6/0407
See application file for complete search history.

(56) References Cited

U.S. PATENT DOCUMENTS

| | | | |
|---|---|---|---|
| 4,197,837 A | 4/1980 | Tringali et al. | |
| 4,967,431 A * | 11/1990 | Hargest | A61G 7/05746 5/689 |
| 5,131,106 A * | 7/1992 | Jackson | A61G 13/00 5/607 |
| 5,195,199 A * | 3/1993 | Sereboff | A47C 7/021 5/654 |
| 5,287,577 A | 2/1994 | Bremer et al. | |
| 5,347,668 A * | 9/1994 | Manning | A61G 13/12 5/622 |
| 5,584,085 A | 12/1996 | Banko | |
| 5,661,860 A * | 9/1997 | Heitz | A47C 20/026 5/630 |
| 5,785,669 A * | 7/1998 | Proctor | A47C 7/425 297/284.6 |
| 5,970,548 A * | 10/1999 | Welch | A61G 7/05776 5/710 |
| 6,009,578 A * | 1/2000 | Davis | A47C 7/021 297/219.1 |
| 6,385,802 B1 * | 5/2002 | Roberts | A61G 13/0009 5/612 |
| 7,024,714 B1 * | 4/2006 | Yates | A47C 27/085 5/654 |
| 7,441,294 B2 * | 10/2008 | Mossbeck | A47C 27/082 297/452.41 |
| 8,468,628 B1 * | 6/2013 | Cheng | A47G 9/007 5/632 |
| 9,084,494 B2 * | 7/2015 | Riach | A47C 20/026 |
| 9,089,462 B1 | 7/2015 | Lafleche | |
| 9,776,724 B2 * | 10/2017 | Marappan | B64D 11/0647 |
| 9,877,588 B2 * | 1/2018 | Belleh | A47C 16/00 |
| 2006/0037142 A1 * | 2/2006 | Binder | A47G 9/10 5/644 |
| 2007/0272450 A1 * | 11/2007 | Skinner | A61G 7/05769 177/144 |
| 2007/0283496 A1 * | 12/2007 | Skripps | A61G 7/05738 5/654 |
| 2008/0028536 A1 * | 2/2008 | Hadden-Cook | A47C 21/044 5/724 |
| 2008/0092295 A1 * | 4/2008 | Flick | A61G 7/05776 5/600 |
| 2009/0100604 A1 * | 4/2009 | Caminade | A61G 7/05776 5/713 |
| 2009/0100605 A1 * | 4/2009 | Caminade | A61G 7/05776 5/713 |
| 2009/0132013 A1 * | 5/2009 | Amalfi | A61F 7/10 607/96 |
| 2009/0192364 A1 * | 7/2009 | Voto | A61B 5/024 600/301 |
| 2010/0024132 A1 * | 2/2010 | Carlson | A61G 7/05776 5/710 |
| 2010/0063638 A1 * | 3/2010 | Skinner | A61G 7/05769 700/281 |
| 2010/0101026 A1 * | 4/2010 | Papaioannou | A61G 7/0573 5/710 |
| 2010/0132120 A1 * | 6/2010 | Koerlin | A61G 5/1043 5/654 |
| 2011/0048429 A1 * | 3/2011 | Callahan | A61G 13/1205 128/845 |
| 2011/0068939 A1 * | 3/2011 | Lachenbruch | A61B 5/002 340/626 |
| 2011/0083275 A1 * | 4/2011 | Glass | A61G 5/1043 5/654 |
| 2011/0191960 A1 * | 8/2011 | Hiebert | A61F 5/05833 5/615 |
| 2011/0289683 A1 * | 12/2011 | Mikkelsen | A47C 21/048 5/421 |
| 2012/0012277 A1 * | 1/2012 | Lachenbruch | A47C 21/044 165/60 |
| 2012/0030878 A1 | 2/2012 | Davenport et al. | |
| 2012/0284923 A1 * | 11/2012 | Jensen | A61G 1/00 5/627 |
| 2012/0311790 A1 * | 12/2012 | Nomura | A61G 7/05776 5/710 |
| 2013/0255699 A1 * | 10/2013 | Squitieri | A61F 5/34 128/892 |
| 2013/0283526 A1 * | 10/2013 | Gagliardi | A61G 13/0009 5/421 |
| 2014/0009293 A1 * | 1/2014 | Sauser | A61B 5/6891 340/573.4 |
| 2014/0013514 A1 * | 1/2014 | Misaki | A61G 7/05769 5/710 |
| 2014/0059781 A1 * | 3/2014 | Lafleche | A47C 27/083 5/713 |
| 2014/0075673 A1 * | 3/2014 | Weedling | A61B 5/0555 5/601 |
| 2014/0101861 A1 | 4/2014 | Gowda et al. | |
| 2014/0202557 A1 * | 7/2014 | Bullin | A61G 7/05776 137/224 |
| 2014/0284988 A1 * | 9/2014 | Gefen | A47C 4/52 297/452.41 |
| 2014/0345058 A1 * | 11/2014 | Escobedo | A61G 7/05769 5/655.3 |
| 2014/0346836 A1 * | 11/2014 | Briggs | A61G 5/14 297/452.41 |
| 2015/0209206 A1 * | 7/2015 | Bargellini | A61G 5/1043 297/217.2 |
| 2015/0238378 A1 * | 8/2015 | Bhat | A61G 7/05776 5/421 |
| 2015/0250670 A1 * | 9/2015 | O'Reagan | A61G 7/057 5/421 |
| 2016/0007764 A1 * | 1/2016 | Fournie | A47C 27/10 137/12 |
| 2016/0022521 A1 * | 1/2016 | Darnold | A61G 7/05776 700/283 |
| 2016/0183693 A1 * | 6/2016 | Shih | A47C 27/121 5/655.5 |
| 2016/0354573 A1 * | 12/2016 | Buswell | A61G 11/00 |
| 2017/0028218 A1 * | 2/2017 | De Neve | A61B 6/0435 |
| 2017/0252246 A1 * | 9/2017 | Egelund | A47C 20/02 |
| 2018/0003684 A1 * | 1/2018 | Kerr | G01N 33/0006 |
| 2018/0073948 A1 * | 3/2018 | Moniaci | G01L 19/0038 |

FOREIGN PATENT DOCUMENTS

WO 2005007054 A1 1/2005
WO 2007146059 A2 12/2007

OTHER PUBLICATIONS

Extended European Search Report dated Oct. 13, 2016 for EP Patent Application No. 16174273.9.

* cited by examiner

SPINE TABLE POSITIONER PAD WITH PRESSURE SENSING AND COOLING FEATURES

CROSS-REFERENCE TO RELATED APPLICATIONS

The present application claims priority to U.S. Provisional Patent Application Ser. No. 62/175,607 filed Jun. 15, 2015 and entitled "SPINE TABLE POSITIONER PAD WITH PRESSURE SENSING AND COOLING FEATURES," the entirety of which is incorporated by reference herein.

TECHNICAL FIELD

The present specification generally relates to spine table positioner pads, and more specifically, to spine table positioner pads having pressure sensing and cooling features.

BACKGROUND

Conventionally, a person is positioned on a spine table for spinal surgery. The spine table includes a number of individual pads to provide modular support to the person. The modular support enables a surgeon to position the person so as to provide access to the portion of the person's spine that is to be operated on. For example, the person can be positioned such that his or her spine is curved or arced, or such that his or her spine is substantially horizontal. However, the modular support pads often apply pressure to where the person's body does not usually receive pressure, such as the chest and hips. The application of pressure in these locations over an extended period of time, such as the length of time to complete an extensive spinal surgery, can lead to the development of pressure ulcers.

In addition, the area in contact with the modular support pads can increase in temperature during the surgery, and moisture may become trapped between the pad and the skin. Increased temperature and moisture can also lead to the development of pressure ulcers.

Accordingly, a need exists for modular support pads that include cooling and pressure sensing features.

SUMMARY

According to some embodiments of the present disclosure, a modular support pad includes a support cushion, a fluid-filled bladder coupled to an electronic pressure sensor for sensing a fluid pressure within the fluid-filled bladder, and a ticking surrounding the support cushion and the fluid-filled bladder and forming a person support surface and a bottom surface.

According to some embodiments of the present disclosure, a modular support system includes a frame; and at least one modular support pad positioned on the frame. The at least one modular support pad includes a support cushion, a fluid-filled bladder coupled to an electronic pressure sensor for sensing a fluid pressure within the fluid-filled bladder, and a ticking surrounding the support pad and the fluid-filled bladder and forming a person support surface and a bottom surface.

According to some embodiments, a method of sensing a pressure applied by a support pad includes positioning a support pad beneath a person. The support pad includes a fluid-filled bladder and a support cushion. The fluid-filled bladder is positioned between the person and the support cushion. The method also includes sensing a fluid pressure within the fluid-filled bladder using an electronic pressure sensor, and adjusting a position of the person or the support pad responsive to the fluid pressure.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
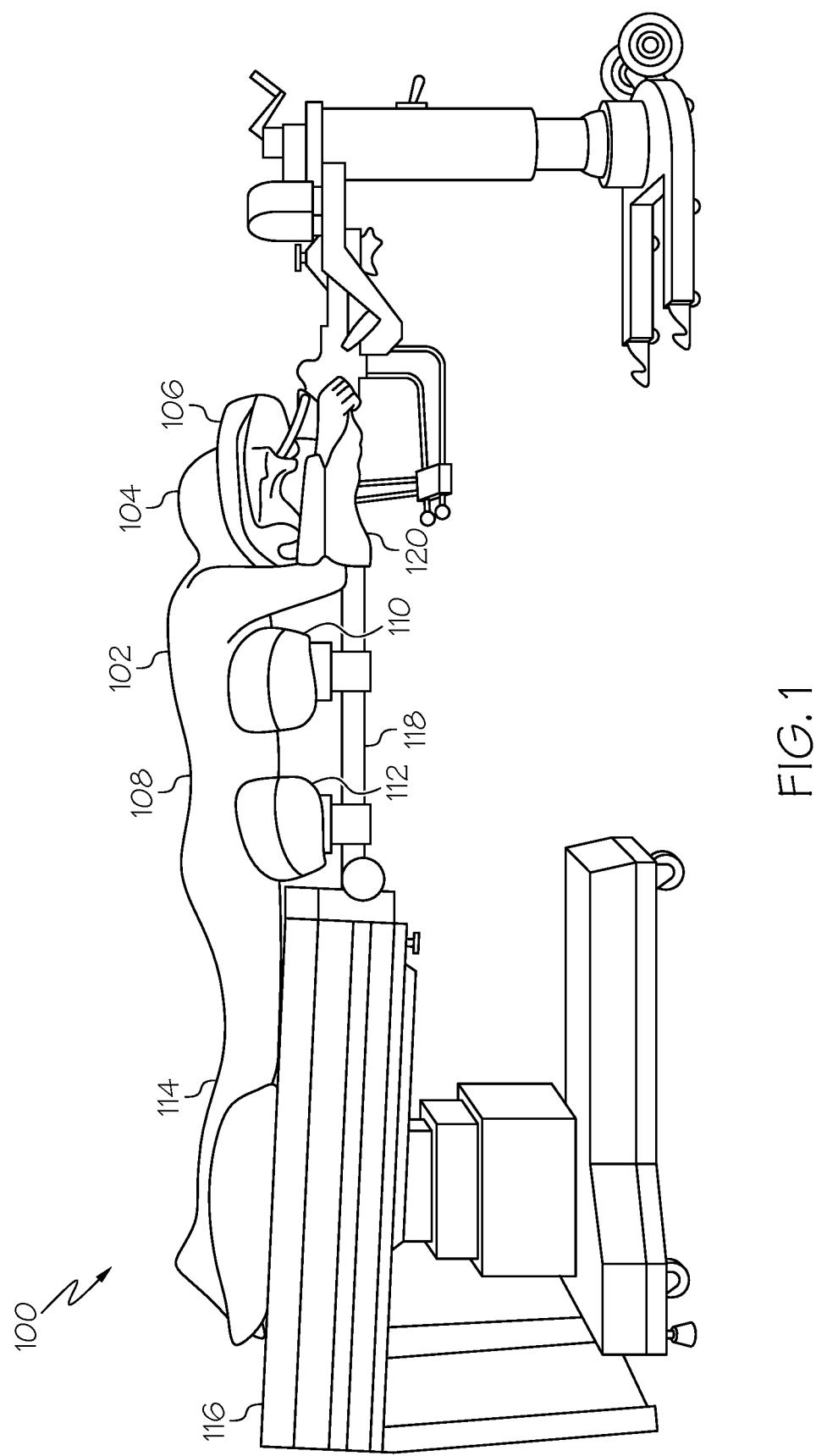
FIG. 1 schematically depicts a spine table in accordance with one or more embodiments.

FIG. 1 generally depicts one embodiment of a spine table including support pads having pressure-sensing and/or cooling features. As will be described, a support pad generally includes a support cushion, a fluid-filled bladder, and a ticking surrounding the support pad and the fluid-filled bladder and forming a person support surface and a bottom surface. In embodiments in which the support pad includes pressure-sensing features, the fluid-filled bladder is coupled to an electronic pressure sensor for sensing a fluid pressure within the fluid-filled bladder. In embodiments in which the support pad includes cooling features, the fluid-filled bladder is coupled to an electronic pump for circulating a cooling fluid within the fluid-filled bladder. Various embodiments of the support pads and methods of using the support pads will be described in more detail herein.

FIG. 1 depicts a modular support system in the form of a spine table 100 supporting a person 102. The person's head 104 is supported by a head positioner 106 of the spine table 100. In various embodiments, the head positioner 106 is annular in shape to accommodate the person's nose and other facial features. The person's torso 108 is supported by one or more chest support pads 110 and one or more hip support pads 112. FIG. 1 also illustrates the person's legs 114 supported by a table 116. The head positioner 106, the one or more chest support pads 110, the one or more hip support pads 112, and the table 116 may be coupled by a frame 118. In various embodiments, the head positioner 106, the one or more chest support pads 110, and the one or more hip support pads 112 may be repositioned along the frame 118 to accommodate persons of varying sizes or in various positions or orientations.

The spine table 100 of FIG. 1 also includes arm pads 120. Like the other pads, the arm pads 120 may be positioned along the frame 118 to support the arms of a person 102 positioned on the spine table 100. In various embodiments, the spine table 100 may include additional accessories or support pads to assist in positioning the person 102 for surgery. For example, additional support pads may be utilized to position the person 102 on one side. As another example, in some embodiments, the table 116 may be replaced by one or more thigh support pads, shin support pads, and/or ankle support pads.

Figure 2:
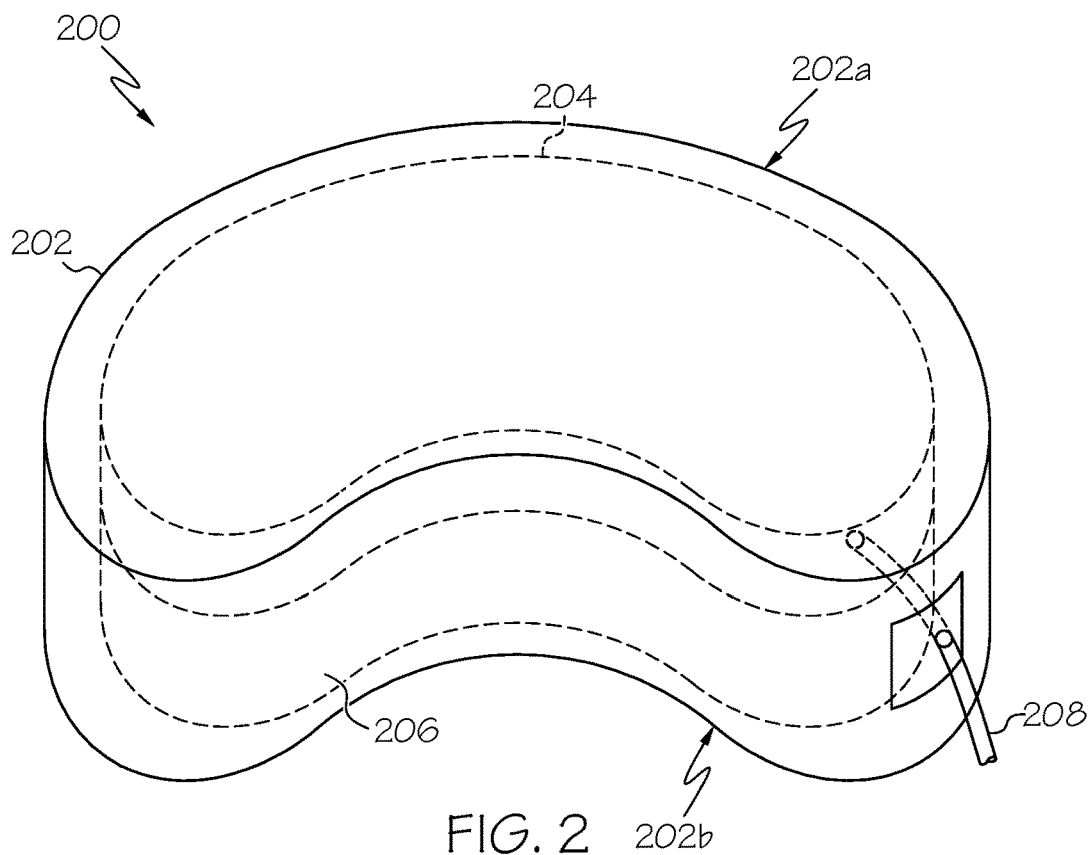
FIG. 2 schematically depicts a support pad including a fluid-filled bladder for pressure sensing in accordance with one or more embodiments.

In various embodiments, one or more of the chest support pads 110, hip support pads 112, or other support pads may include pressure-sensing and/or cooling features. As shown in FIG. 2, a support pad 200 generally includes a ticking 202 covering one or more fluid-filled bladders 204 and a support cushion 206, both shown in phantom. Although the support pad 200 depicted in FIG. 2 includes a single fluid-filled bladder 204, in some embodiments, the support pad 200 may include two or more chambers within the fluid-filled bladder 204. As used herein, "chambers" may refer to individual compartments within a single fluid-filled bladder, or to discrete fluid-filled bladders within the support pad 200. In various embodiments, the ticking 202 is made of a wipeable material, such as nylon coated with polyurethane. Other materials may be used, depending on the particular embodiment. For example, materials selected for use may be moisture and vapor permeable but liquid impermeable to allow the material to wick moisture away from the skin of the person positioned on the support pad. In various embodiments, the ticking 202 is a low friction, air permeable material (such as spandex, nylon, or similar materials) that allows the ticking 202 to move in response to the motion of a person on the support pad 200, in order to reduce shear forces, for instance. In other embodiments, the ticking 202 is made of a non-air permeable, moisture/vapor permeable material such as Teflon or urethane-coated fabric. As shown in FIG. 2, the ticking 202 forms a person support surface 202a and a bottom surface 202b.

In various embodiments, the fluid-filled bladder 204 acts as a transducer to measure changes in pressure. For example, the fluid-filled bladder 204 may be calibrated such that any changes in pressure are attributable to the pressure being applied to a person supported by the support pad 200. In various embodiments, the fluid-filled bladder 204 is formed from a membrane that deforms in response to pressure. The membrane is made of a radiolucent, fluid-proof material that prevents the fluid contained within the fluid-filled bladder from escaping through the membrane. For example, the membrane may be a thin plastic or polymeric material. The fluid contained within the fluid-filled bladder may be an oil, water, or other stable aqueous composition that does not compress. In various embodiments, the fluid within the fluid-filled bladder 204 is pressurized. In such embodiments, the pressure of the fluid within the fluid-filled bladder 204 may be adjusted to achieve a predetermined pressure. For example, the pressure of the fluid may be decreased to reduce a pressure, which may increase blood flow to the area of the person in contact with the support pad 200. Alternatively, the pressure of the fluid may be increased to increase a pressure, which may provide additional support to the person in contact with the support pad 200. The pressure of the fluid within the fluid-filled bladder may be controlled, for example, by a fluid pump.

According to various embodiments, when pressure is applied to the fluid-filled bladder 204, such as when a person is positioned on the support pad 200, the membrane deforms and pushes a volume of the fluid out of the fluid-filled bladder 204 and the support pad 200 via tubing 208. In various embodiments, the tubing 208 is a radiolucent material, such as plastic tubing. The tubing 208 is connected to an electronic pressure sensor 210 (shown in FIG. 3) to sense the fluid pressure and output a signal corresponding to the applied pressure.

Figure 3:
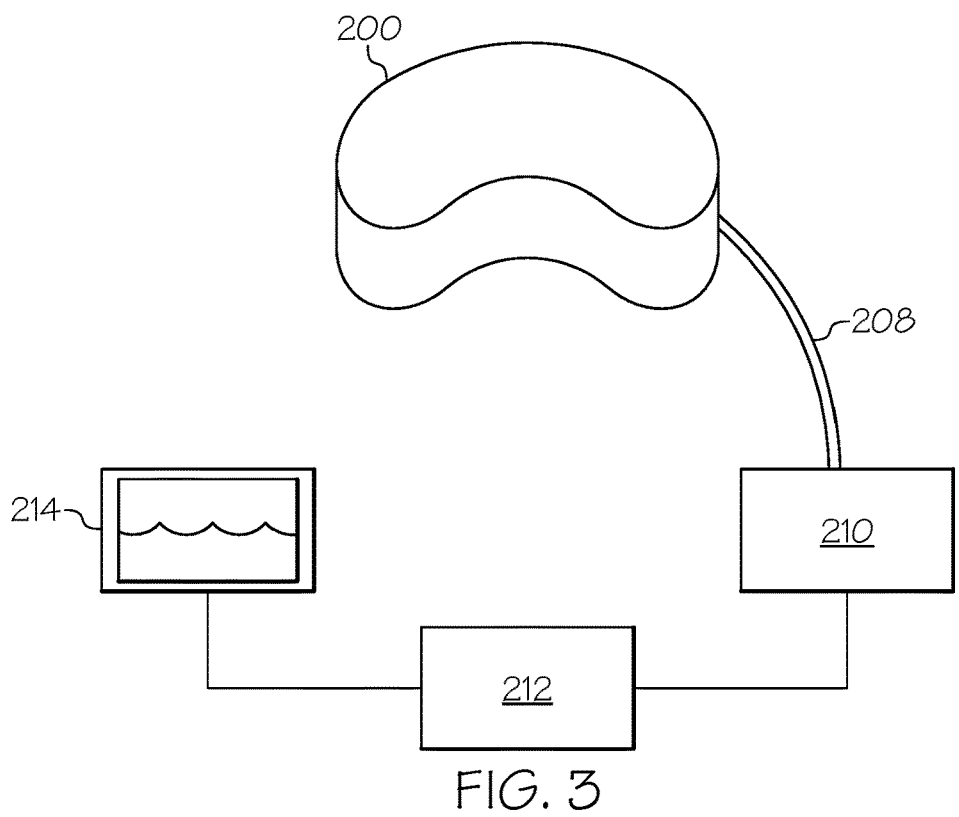
FIG. 3 schematically depicts a pressure sensing circuit including a support pad in accordance with one or more embodiments.

As shown in FIG. 3, in various embodiments, the electronic pressure sensor 210 is located external to the support pad 200 and is connected to the tubing 208. The electronic pressure sensor 210 senses the pressure in the tubing 208 as a result of the fluid entering the tubing 208 and converts the pressure into an electrical signal. More specifically, fluid entering the tubing 208 alters the reading by the electronic pressure sensor 210, which is interpreted as a change in pressure. In various embodiments, the electronic pressure sensor 210 provides an output corresponding to the applied pressure. For example, the electronic pressure sensor 210 may be coupled to a control system 212 with a display device 214 which displays a graph or numeric value representative of the pressure to be displayed on the display device 214. In some embodiments, the electronic pressure sensor 210 provides an output when the pressure exceeds a predetermined threshold or an acceptable range of pressure values. The acceptable range of pressure values may be a function of the weight of the patient and/or a function of a position of the support pad 200. For example, an acceptable range of pressure values may be higher for a thigh support pad as compared to an acceptable range of pressure values for a head support.

In embodiments in which the support pad 200 includes more than one chamber, each chamber may be coupled to an electronic pressure sensor 210. In various embodiments, the pressure of each chamber may be individually measured and controlled. For example, the control system 212 may be communicatively coupled to a first fluid pump that is configured to adjustably control the pressure of the fluid within a first chamber and a second fluid pump that is configured to adjustably control the pressure of the fluid within a second chamber. Accordingly, the pressure of the fluid within the first chamber may be increased while the pressure of the fluid within the second chamber is decreased, the pressure of the fluid in one of the chambers may be increased or decreased while the pressure of the fluid within the other chamber is maintained, or the like.

When the pressure exceeds the threshold or the acceptable range of pressure values, in various embodiments, a position of the person or the support pad is adjusted. For example, the support pad can be moved along the frame 118 and/or the person may be repositioned on the spine table to reduce the fluid pressure to an acceptable pressure value. Alternatively or in addition, fluid may be added to or removed from the fluid-filled bladder 204, or the pressure of the fluid may be increased or decreased, to increase or decrease the pressure of the support pad 200.

According to various embodiments, the electronic pressure sensor 210 is calibrated at ambient temperature and pressure. For example, prior to positioning a person on support pad 200, the electronic pressure sensor 210 may be zeroed such that any increase in pressure is attributed to the weight of the person positioned on the support pad 200. In various embodiments, calibration further includes placing one or more known weights on the support pad 200 and sensing the fluid pressure using the electronic pressure sensor 210. The sensed fluid pressure may be recorded in some embodiments.

As shown in FIG. 2, the support pad 200 also includes a support cushion 206. The support cushion 206 may be a foam or other cushioning material that provides support to a person positioned on the support pad 200. In various embodiments, the fluid-filled bladder 204 is positioned between the support cushion 206 and the person support surface 202*a*. This configuration enables the fluid-filled bladder 204 to function as a pressure transducer without concern that the support cushion 206 has attenuated some or all of the pressure.

During spinal surgery, a surgeon may use x-rays or other imaging techniques to assist with visualization of the surgical area. It should be appreciated that various embodiments of the support pad 200 employ radiolucent materials. Accordingly, the support pad 200, and the pressure transducer in the form of the fluid-filled bladder 204, do not adversely affect x-rays taken during treatment of the person.

Figure 4:
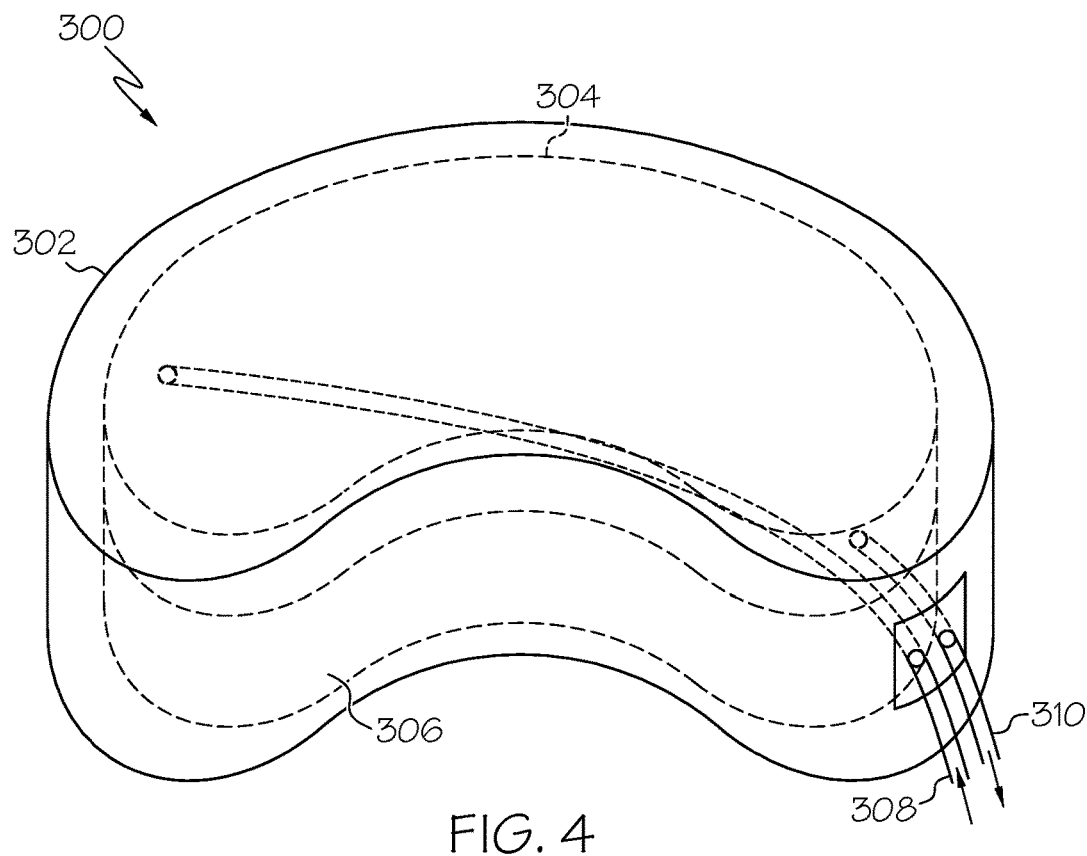
FIG. 4 schematically depicts a support pad including a fluid-filled bladder for cooling in accordance with one or more embodiments.

Turning now to FIG. 4, an alternative embodiment of a support pad 300 is shown. In FIG. 4, support pad 300 generally includes a ticking 302 covering a bladder 304 and a support cushion 306, both shown in phantom. In various embodiments, the bladder 304 is coupled to an electronic pump 312 (shown in FIG. 5) for circulating a cooling fluid within the bladder 304. More specifically, the electronic pump 312 may direct cooling fluid into the bladder 304 through the inlet tube 308. The cooling fluid may circulate within the bladder 304 before exiting the bladder 304 via the outlet tube 310. In some embodiments, the cooling fluid may be pumped into the bladder 304 at one end and exit the bladder 304 at another end of the bladder 304 opposing the first end. However, in other embodiments, tubing or another passageway may be provided within the bladder 304 to direct the cooling fluid through the bladder 304.

As used herein, a "cooling fluid" may be any suitable gas or liquid. In various embodiments, the cooling fluid may be an oil, water, or other stable fluid composition that has high thermal capacity and low viscosity. In some embodiments, the cooling fluid may be glycol or a fluid that does not freeze at operating temperatures. According to various embodiments, the cooling fluid is pumped into the bladder 304 at a temperature from about 28° C. to about 32° C. In some embodiments, the cooling fluid may have a temperature as low as about 15.5° C. when it enters the bladder 304. The temperature of the cooling fluid may vary depending on the particular embodiment.

Figure 5:
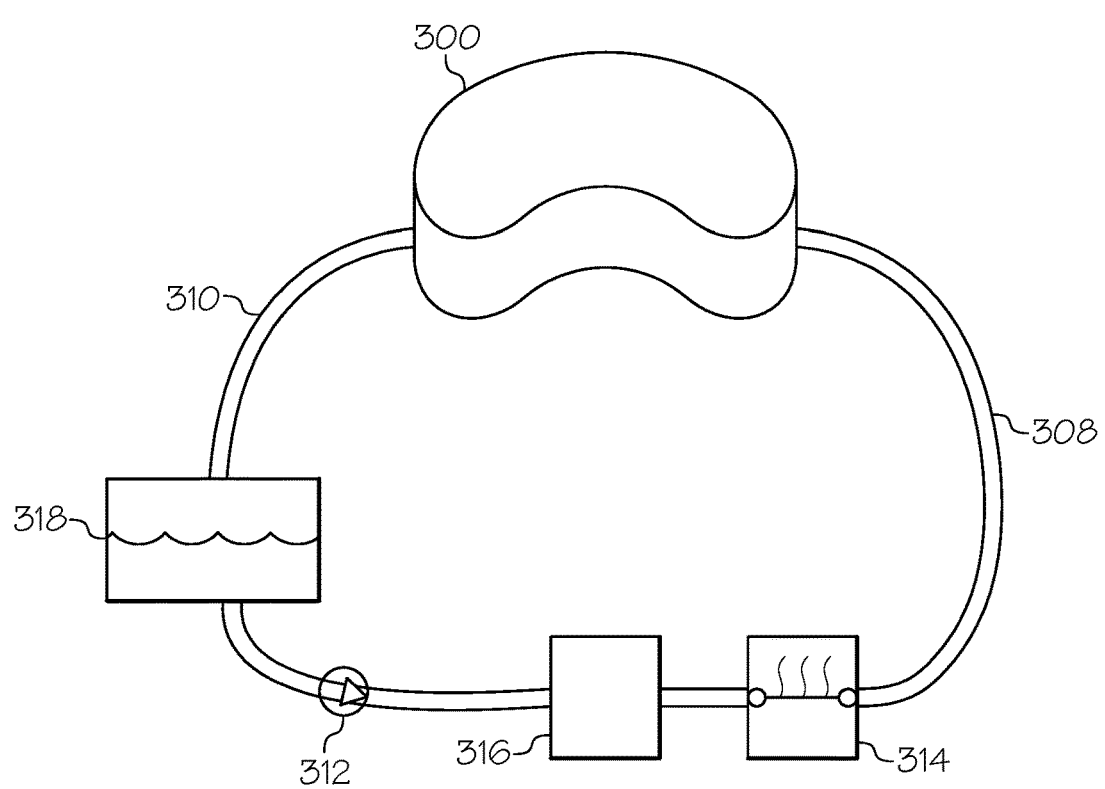
FIG. 5 schematically depicts a cooling circuit including a support pad in accordance with one or more embodiments.

As shown in FIG. 5, in order to cool the cooling fluid to the desired temperature, various embodiments include a heat sink 314 and/or a Peltier cooler 316. The heat sink 314 and/or Peltier cooler 316 cool the cooling fluid before it is circulated through the bladder 304. Accordingly, in various embodiments, the heat sink 314 and/or Peltier cooler 316 are located external to the bladder 304 and the support pad 300. FIG. 5 also depicts a reservoir 318 holding a supply of cooling fluid. A thermostat may be included as part of the electronic pump 312 or may be incorporated as a separate component.

As the cooling fluid is circulated through the bladder 304 of the support pad 300, the cooling fluid removes heat from the fluid in the bladder imparted to the fluid by the person supported by the support pad 300. In various embodiments, the cooling fluid is effective to reduce the temperature of the person to a temperature from about 35° C. to about 36° C.

As with support pad 200, it should be appreciated that various embodiments of the support pad 300 employ radiolucent materials. Accordingly, the support pad 300 and the bladder 304 do not adversely affect x-rays taken during treatment of the person. Moreover, the heat sink 314 and/or Peltier cooler 316, the electronic pump 312, and other components that may adversely affect x-rays are located external to from the support pad 300.

FIGS. 2 and 4 illustrate support pads including either a pressure-sensing fluid-filled bladder or a cooling bladder. However, still other embodiments may include both pressure-sensing and cooling capabilities. For example, the fluid-filled bladder 204 of FIG. 2 may be filled with a cooling fluid. Alternatively or in addition, the fluid-filled bladder 204 of FIG. 2 may include tubing throughout the fluid-filled bladder 204 to circulate cooling fluid. The cooling fluid may be the same as the fluid used for determining pressure, or may be a different fluid isolated from the fluid for determining pressure. In still other embodiments, a cooling bladder, such as bladder 304 may be used in addition to the fluid-filled bladder 204. Additional methods of combining cooling and pressure sensing capabilities should be apparent to those skilled in the art.

In various embodiments, a method of sensing a pressure applied by a support pad includes positioning a support pad beneath a person, sensing a fluid pressure within the fluid-filled bladder using an electronic pressure sensor; and adjusting a position of the person or the support pad responsive to the fluid pressure. The person or the support pad are adjusted to reduce the fluid pressure. In various embodiments, an output regarding the pressure is provided, such as on a display. Accordingly, the person and/or the support pad may be adjusted to bring the pressure into an acceptable range of pressures.

In one particular embodiment, adjustment of the support pad may include adjusting the pressure of the fluid in one or more chambers within the support pad. For example, the fluid pump may increase or decrease the pressure of the fluid within one or more chambers of the fluid-filled bladder responsive to the fluid pressure.

In another embodiment, the method includes sensing a fluid pressure within a first chamber using a first electronic pressure sensor, sensing a fluid pressure within a second chamber using a second electronic pressure sensor, and adjusting the pressure of at least one of the first and second chambers responsive to the fluid pressure within the first chamber and the fluid pressure within the second chamber.

Various embodiments described herein include a pressure-sensing and/or cooling bladder included in a support pad. The pressure-sensing features may reduce the likelihood of pressure ulcers by providing information regarding pressure being applied to a person supported by the support pad. This information may be utilized by caregivers, such as nurses and surgeons, to reposition the person effective to reduce the pressure to a suitable level. Similarly, the cooling features may reduce a temperature of the tissue in contact with the support pad, which may further reduce the likelihood of a pressure ulcer. In various embodiments, the support pad is made of radiolucent materials to enable the support pad to be used without interfering with imaging techniques utilized while the support pads are in use.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method of sensing a pressure applied by a support pad, the method comprising:
positioning a support pad beneath a person, the support pad comprising a fluid-filled bladder containing a fluid comprising an oil, water, or other stable aqueous composition comprising one or more chambers, a support cushion, the fluid-filled bladder positioned between the person and the support cushion;
sensing a fluid pressure via tubing within each of the one or more chambers of the fluid-filled bladder based on an amount of the oil, water, or other stable aqueous composition entering the tubing with an electronic pressure sensor positioned external to the support pad; and
adjusting a position of the support pad horizontally along a frame relative to the person responsive to the fluid pressure.

2. The method according to claim 1, wherein adjusting the position of the support pad reduces the fluid pressure.

3. The method according to claim 1, further comprising: circulating a cooling fluid through the fluid-filled bladder.

4. The method according to claim 1, further comprising: providing an output related to the fluid pressure.

5. The method according to claim 1, further comprising adjusting a pressure of the fluid within at least one of the one or more chambers of the fluid-filled bladder while maintaining the pressure of the fluid within another of the one or more chambers of the fluid-filled bladder.

* * * * *